United States Patent
Hansen et al.

(10) Patent No.: US 8,557,553 B2
(45) Date of Patent: Oct. 15, 2013

(54) NUCLEASE REDUCTION

(75) Inventors: Kim Uhre Hansen, Hilleroed (DK); Peter Rahbek Oestergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 418 days.

(21) Appl. No.: 12/671,973

(22) PCT Filed: Aug. 19, 2008

(86) PCT No.: PCT/EP2008/060855
§ 371 (c)(1),
(2), (4) Date: Feb. 3, 2010

(87) PCT Pub. No.: WO2009/024574
PCT Pub. Date: Feb. 26, 2009

(65) Prior Publication Data
US 2011/0229954 A1    Sep. 22, 2011

Related U.S. Application Data

(60) Provisional application No. 60/956,941, filed on Aug. 21, 2007.

(30) Foreign Application Priority Data

Aug. 20, 2007   (EP) .................................. 07114613

(51) Int. Cl.
*C12N 9/96* (2006.01)
*C07K 1/02* (2006.01)
*C07K 1/113* (2006.01)
*C12N 9/54* (2006.01)

(52) U.S. Cl.
USPC ............................. 435/188; 435/221; 530/412

(58) Field of Classification Search
None
See application file for complete search history.

(56) References Cited

U.S. PATENT DOCUMENTS

| | | | |
|---|---|---|---|
| 3,623,957 A | | 11/1971 | Feldman |
| 4,569,911 A | * | 2/1986 | Tsuda ........................... 435/109 |
| 6,207,437 B1 | * | 3/2001 | Gros et al. .................... 435/220 |
| 2004/0241664 A1 | * | 12/2004 | Dekker et al. ..................... 435/6 |
| 2005/0014169 A1 | * | 1/2005 | Latham et al. .................... 435/6 |
| 2006/0188892 A1 | * | 8/2006 | Latham et al. .................... 435/6 |

FOREIGN PATENT DOCUMENTS

| | | |
|---|---|---|
| EP | 0 549 048 | 6/1993 |
| WO | WO 98/04730 | 2/1998 |
| WO | WO 02/08398 | 1/2002 |

OTHER PUBLICATIONS

Finlayson et al., "Preparation of a Nuclease-Free Alpha Amylase and its Use in DNA Purification", Biotechnology Techniques, vol. 6, No. 1, pp. 53-54, 1992.
Tullis et al., "Calcium Protects DNase I From Proteinase K A New method for the Removal of Contaminating RNase from DNase I", Analytical Biochemistry, vol. 107, No. 1, pp. 260-264, 1980.
International Search Report issued in corresponding international application No. PCT/EP2008/060855 dated Nov. 25, 2008.

* cited by examiner

*Primary Examiner* — Nashaat Nashed
*Assistant Examiner* — William W Moore
(74) *Attorney, Agent, or Firm* — Michael W. Krenicky

(57) ABSTRACT

The present disclosure relates to a method for reducing nuclease activity in a subtilisin solution obtained from a fermentation broth including: a) adjusting the pH of the subtilisin solution to a pH in the range of from pH 8.5 to pH 10.5; b) adding a polyol; and c) adjusting the temperature of the subtilisin solution to a temperature in the range of from 50° C. to 80° C. In accordance with the present disclosure, the nuclease activity is reduced to less than 5% of the initial value and the subtilisin activity is maintained at more than 60% of the initial value.

21 Claims, No Drawings

NUCLEASE REDUCTION

CROSS-REFERENCE TO RELATED APPLICATIONS

This application is a 35 U.S.C. 371 national application of PCT/EP2008/060855 filed Aug. 19, 2008, which claims priority or the benefit under 35 U.S.C. 119 of European application no. EP 07114613.8 filed Aug. 20, 2007 and U.S. provisional application No. 60/956,941 filed Aug. 21, 2007, the contents of which are fully incorporated herein by reference.

FIELD OF INVENTION

The present invention provides a method of inactivating the nuclease activity and keeping most of the subtilisin activity in a subtilisin solution obtained from a fermentation broth.

BACKGROUND

Nuclease activity is ubiquitous in nature and is normally present in any fermentation broth. Some nucleases are known to be very stable.

Sometimes it is very important that the subtilisin product obtained from a fermentation broth is without nuclease activity; e.g., if the subtilisin product is to be used for removal of nucleases when isolating DNA and RNA from tissues or cell lines or if the subtilisin product is to be used for isolating PCR or RT-PCR templates.

It is known from "Biotechnology Techniques, Vol. 6, No. 1, 1992, p. 53-54" that a thermostable alpha-amylase when heated to 80° C. for 20 minutes may retain >90% of its activity and at the same time lose all DNAase activity.

Subtilisins are normally not able to tolerate such a long heat treatment at 80° C. and will lose a significant part of its activity.

Our inventors have found an improved method of inactivating the nuclease activity and keeping most of the subtilisin activity.

SUMMARY OF THE INVENTION

The present inventors have found that it is possible to inactivate the nuclease activity and keep most of the subtilisin activity in a subtilisin solution obtained from a fermentation broth, so we claim:
A method for reducing nuclease activity in a subtilisin solution obtained from a fermentation broth comprising
a) adjusting the pH of the subtilisin solution to a pH in the range of from pH 8.5 to pH 10.5;
b) adding a polyol;
c) adjusting the temperature of the subtilisin solution to a temperature in the range of from 50° C. to 80° C.;
whereby the nuclease activity is reduced to less than 5% of the initial value and the subtilisin activity is maintained at more than 80% of the initial value.

DETAILED DESCRIPTION

Nucleases

The nuclease may be any nuclease that the microorganism producing the subtilisin of interest also produces or it may be an exogenous nuclease which has contaminated the subtilisin product during the preparation of the subtilisin product. The nuclease may be a ribonuclease (RNase) or a deoxyribonuclease (DNase), in particular a ribonuclease (RNase).

The nuclease activity may be measured using any assay known in the art, e.g., the RNase activity assay described in Example 1.

Subtilisins

The present invention deals with subtilisins. A subtilisin includes, but is not limited to, any enzyme belonging to the NC-IUBMB enzyme classification: EC 3.4.21.62.

In this patent application we define a subtilisin as a peptidase, which according to the MEROPS peptidase classification is described as: Clan SB, Family S8A.

Subtilisins are described in, e.g., Barrett et al. 1998. Handbook of proteolytic enzymes. Academic press, p. 289-294.

The protease activity can be measured using any assay, in which a substrate is employed, that includes peptide bonds relevant for the specificity of the protease in question. Assay-pH and assay-temperature are likewise to be adapted to the protease in question.

There are no limitations on the origin of the subtilisin of the invention and/or for the use according to the invention. Thus, the term subtilisin includes not only natural or wild-type subtilisins, but also any mutants, variants, fragments etc. thereof exhibiting protease activity, as well as synthetic proteases, shuffled proteases, and consensus proteases.

Such genetically engineered proteases can be prepared as is generally known in the art, e.g., by Site-directed Mutagenesis, by PCR (using a PCR fragment containing the desired mutation as one of the primers in the PCR reactions), or by Random Mutagenesis. The preparation of consensus proteins is described in, e.g., EP 897985.

A preferred subtilisin is a subtilisin selected from the group consisting of subtilisin Carlsberg, subtilisin BPN', subtilisin 147, subtilisin 309 and subtilisin 1168, including any mutants, variants, fragments etc. thereof exhibiting protease activity. The amino acid sequences of these 5 subtilisins are all described in WO 89/06279.

Preferred commercially available subtilisins include ALCALASE™, SAVINASE™, ESPERASE™, EVERLASE™, OVOZYME™, CORONASE™, POLARZYME™, KANNASE™, LIQUANASE™, and RELASE™ (Novozymes A/S), MAXATASE™, MAXACAL™ MAXAPEM™, PROPERASE™, PURAFECT™, PURAFECT OXP™, FN2™, FN3™ and FN4™ (Genencor International Inc.).

Microorganism Producing the Subtilisin of Interest

According to the invention the subtilisin of interest is preferably produced in a *Bacillus* species. Preferably the *Bacillus* species is selected from the group consisting of *Bacillus alkalophilus, Bacillus amyloliquefaciens, Bacillus brevis, Bacillus circulans, Bacillus clausii, Bacillus coagulans, Bacillus halodurans, Bacillus lautus, Bacillus lentus, Bacillus licheniformis, Bacillus megaterium, Bacillus pumilus, Bacillus stearothermophilus, Bacillus subtilis*, and *Bacillus thuringiensis*. Preferably the subtilisin of interest is produced in *Bacillus clausii, Bacillus lentus, Bacillus licheniformis*, or *Bacillus subtilis*.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Fermentation Broth

The microorganism producing the subtilisin of interest may be fermented by any method known in the art. The fermentation medium may be a minimal medium as described in, e.g., WO 98/37179, or the fermentation medium may be a complex medium comprising complex nitrogen and carbon sources, wherein the complex nitrogen source may be partially hydrolysed as described in WO 2004/003216.

The fermentation may be performed as a batch, a repeated batch, a fed-batch, a repeated fed-batch or a continuous fermentation process.

In a fed-batch process, either none or part of the compounds comprising one or more of the structural and/or catalytic elements is added to the medium before the start of the fermentation and either all or the remaining part, respectively, of the compounds comprising one or more of the structural and/or catalytic elements are fed during the fermentation process. The compounds which are selected for feeding can be fed together or separate from each other to the fermentation process.

In a repeated fed-batch or a continuous fermentation process, the complete start medium is additionally fed during fermentation. The start medium can be fed together with or separate from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth.

Fermentation/Recovery Steps

The subtilisin of interest may be fermented by methods known in the art, e.g., as described in U.S. Pat. No. 3,723,250.

The subtilisin of interest is not limited to, but will typically be recovered by using some or all of the following steps:

1) pre-treatment of broth
2) removal of cells and other solid material from broth (primary separation)
3) filtration
4) concentration (e.g., ultrafiltration, crystallization, evaporation)
4b) New step: Nuclease inactivating step
5) filtration
6) further purification (e.g., salt precipitation, chromatography)
7) stabilization and standardization.

In the pre-treatment step, cells and solid material are flocculated and some soluble components are precipitated. This step may be carried out as described in WO 96/38469. The removal of cells and other solid material may be carried out by centrifugation, filtration, or micro filtration.

The filtration step may be included in order to improve the clarity of the subtilisin solution and/or to remove microbial cells. The concentration step will typically involve an ultrafiltration step or an evaporation of water at reduced pressure. During the concentration, solid material may be formed which can be removed by further filtrations. Finally, the subtilisin product may be further purified, stabilized and standardized to the desired concentration as known in the art.

Apart from the unit operations listed above, a number of other recovery procedures and steps may be applied, e.g., treatment of the subtilisin solution with active carbon, and/or use of various adsorbents, e.g., to remove undesired compounds such as side-activities and coloured compounds.

The nuclease inactivating step according to the present invention will typically take place after the concentration step.

Nuclease Inactivating Process

The pH of the subtilisin solution obtained from the fermentation broth (typically after a flocculation, a centrifugation and an ultrafiltration) is then adjusted to a pH value in the range of from pH 8.5 to pH 10.5, in particular to a pH value in the range of from pH 9.0 to pH 10.0.

One or more polyols are then added. The polyol(s) may be added before, simultaneously or after the adjustment of the pH adjustment.

The temperature of the subtilisin solution obtained from the fermentation broth is then adjusted to a temperature in the range of from 50° C. to 80° C., preferably to a temperature in the range of from 55° C. to 75° C., more preferably to a temperature in the range of from 60° C. to 70° C., in particular to a temperature in the range of from 63° C. to 67° C.

The subtilisin solution may typically be incubated at the high pH and at the high temperature for a period of up to 30 minutes; preferably for a period of up to 15 minutes, more preferably for a period of up to 10 minutes, in particular for a period of up to 5 minutes.

By using the combination of a polyol, high pH and high temperature the nuclease activity is reduced to less than 5% of the initial value, preferable the nuclease activity is reduced to less than 4% of the initial value, more preferably the nuclease activity is reduced to less than 3% of the initial value, even more preferably the nuclease activity is reduced to less than 2% of the initial value, in particular the nuclease activity is reduced to less than 1% of the initial value, especially the nuclease activity is reduced to less than 0.5% of the initial value.

By using the combination of a polyol, high pH and high temperature the subtilisin activity is maintained at more than 80% of the initial value, preferably the subtilisin activity is maintained at more than 90% of the initial value, more preferably the subtilisin activity is maintained at more than 91% of the initial value, more preferably the subtilisin activity is maintained at more than 92% of the initial value, more preferably the subtilisin activity is maintained at more than 93% of the initial value, more preferably the subtilisin activity is maintained at more than 94% of the initial value, more preferably the subtilisin activity is maintained at more than 95% of the initial value, more preferably the subtilisin activity is maintained at more than 96% of the initial value, more preferably the subtilisin activity is maintained at more than 97% of the initial value, more preferably the subtilisin activity is maintained at more than 98% of the initial value, more preferably the subtilisin activity is maintained at more than 99% of the initial value, in particular the subtilisin activity is maintained at more than 99.5% of the initial value.

Polyols

Any polyol may be used according to the invention. However, a polyol selected from the group consisting of 1,2-propandiol (monopropylene glycol or MPG), 1,3-propandiol, glycerol, ethylene glycol, xylitol, arabitol, dulcitol, mannitol, erythritol, cellobiose and sorbitol, is preferred, in particular MPG.

The polyol may be added in a concentration of from 10% (v/v) to 60% (v/v); preferably in a concentration of from 20% (v/v) to 50% (v/v); in particular in a concentration of from 30% (v/v) to 50% (v/v).

The invention is further illustrated in the following example which is not intended to be in any way limiting to the scope of the invention as claimed.

EXAMPLE 1

Inactivating RNase Activity in a Subtilisin Solution Obtained from a Fermentation Broth Assays:

Subtilisin samples were analyzed for RNase activity using a modified Ambion assay and for protease activity using a Protazyme AK (cross-linked and dyed casein) assay.

RNase Activity Assay:

This assay is slightly modified compared to the RNase detection kit from Ambion Inc.: RNaseAlert QC System (catalog #1966).

Substrate: RNaseAlert Substrate, RNA coupled with a fluorophor and a quencher (supplied with the kit).

Temperature: room temperature.

Assay buffers: 10× NucleaseAlert Buffer and TE Buffer (both supplied with the kit).

RNase free water (supplied with the kit).

RNase decontamination: RNaseZap (supplied with the kit) was used to clean pipettes and the lab. bench just before RNase activity assay was performed.

Fluorometer: PolarStar, with excitation filter=485–P and emission filter=520–12 and parameters: Gain=50, No. cycles=20, Flashes=4, Pos. delay=0.3, Cycle time=30 s.

Substrate (working solution): 1 tube lyophilized RNaseAlert Substrate was dissolved in 1 ml TE buffer (vortex) and diluted 5× with RNase free water.

20 micro liter 10× NucleaseAlert Buffer and 80 micro liter diluted subtilisin sample (diluted in RNase free water) was placed in the well of a black microtiterplate. The assay was started by adding 100 micro liter Substrate (working solution) and the increase in fluorescence was monitored by the PolarStar equipment as a measure of the RNase activity. A buffer blind (RNase free water) was included in the assay (instead of enzyme).

Subtilisin Activity Assay:

Substrate: Protazyme AK tablet (from Megazyme).

Temperature: 37° C.

Assay buffer: 50 mM $H_3BO_3$/NaOH, 0.01% Triton X-100, pH 9.0.

A Protazyme AK tablet (from Megazyme) was suspended in 2.0 ml 0.01% Triton X-100 by gentle stirring. 500 micro liter of this suspension and 500 microliter assay buffer were mixed in an Eppendorf tube and placed on ice. 20 micro liter diluted subtilisin sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 r.p.m.). The incubation was stopped by transferring the tube back to the ice bath. Then the tube was centrifuged in an ice cold centrifuge for a few minutes and 200 micro liter supernatant was transferred to a microtiter plate. $OD_{650}$ was read as a measure of protease activity. A buffer blind was included in the assay (instead of enzyme).

Test A:

Subtilisin 147 was fermented as known in the art.

The fermentation broth was flocculated, centrifuged, and ultrafiltrated as known in the art.

pH of the ultrafiltrated solution was app. 6.5, and the temperature of the ultrafiltrated solution was 20-25° C. (room temperature).

pH of the ultrafiltrated solution was adjusted to pH 9.0 with 27% (w/w) NaOH (with no loss of either RNase activity or subtilisin activity).

200 micro liter of the pH adjusted ultrafiltrated solution was transferred to an Eppendorf tube. At time=0 min, the tube was transferred to an Eppendorf mixer, which was pre-warmed to 70° C. and 1400 r.p.m. The incubation was stopped by removing the tube from the Eppendorf mixer and allowing the tube to reach room temperature (few minutes). The tube was then transferred to an ice bath and kept on ice until measurement of RNAse and subtilisin activity. RNase and subtilisin activity were measured after an incubation time of 0 min., 1 min., 2 min., 4 min., 6 min., and 8 min. The results are shown in Table 1.

TABLE 1

RNase activity and subtilisin activity (pH 9.0 and 70° C.)

| Time | 0 min. | 1 min. | 2 min. | 4 min. | 6 min. | 8 min. |
|---|---|---|---|---|---|---|
| RNase Activity | 100% | 86% | 55% | 8% | 0% | 0% |
| Subtilisin activity | 100% | 100% | 96% | 80% | 70% | 64% |

Conclusion:

It can be seen from Table 1 that if no polyol is added it is possible to inactivate the RNase (0% after 6 min.), but the subtilisin activity is at the same time reduced to 70% of the initial value.

Test B:

Subtilisin 147 was fermented as known in the art.

The fermentation broth was flocculated, centrifuged, and ultrafiltrated as known in the art. pH of the ultrafiltrated solution was app. 6.5, and the temperature of the ultrafiltrated solution was 20-25° C. (room temperature).

pH of the ultrafiltrated solution was adjusted to pH 9.0 with 27% (w/w) NaOH, and MPG was added to a final 50% (v/v) concentration.

200 micro liter of the pH adjusted ultrafiltrated solution was transferred to an Eppendorf tube. At time=0 min, the tube was transferred to an Eppendorf mixer, which was pre-warmed to 70° C. and 1400 r.p.m. The incubation was stopped by removing the tube from the Eppendorf mixer and allowing the tube to reach room temperature (few minutes). The tube was then transferred to an ice bath and kept on ice until measurement of RNAse and subtilisin activity. RNase and subtilisin activity were measured after an incubation time of 0 min., 1 min., 2 min., 4 min., 6 min., and 8 min. The results are shown in Table 2.

TABLE 2

RNase activity and subtilisin activity (pH 9.0 and 70° C.)

| Time | 0 min. | 1 min. | 2 min. | 4 min. | 6 min. | 8 min. |
|---|---|---|---|---|---|---|
| RNase Activity | 100% | 4% | 0% | 0% | 0% | 0% |
| Subtilisin activity | 100% | 102% | 101% | 108% | 105% | 106% |

Conclusion:

It can be seen from Table 2 that by using the method of the invention it is possible to inactivate the RNase completely (0% after 2 min.), and at the same time maintain all the subtilisin activity.

Test C:

Subtilisin 147 was fermented as known in the art.

The fermentation broth was flocculated, centrifuged, and ultrafiltrated as known in the art.

pH of the ultrafiltrated solution was app. 6.5, and the temperature of the ultrafiltrated solution was 20-25° C. (room temperature).
pH of the ultrafiltrated solution was adjusted to pH10.0 with 27% (w/w) NaOH and MPG was added to a final 50% (v/v) concentration.
200 micro liter of the pH adjusted, ultrafiltrated solution was transferred to an Eppendorf tube. At time=0 min, the tube was transferred to an Eppendorf mixer, which was pre-warmed to 70° C. and 1400 r.p.m. The incubation was stopped by removing the tube from the Eppendorf mixer and allowing the tube to reach room temperature (few minutes). The tube was then transferred to an ice bath and kept on ice until measurement of RNAse and subtilisin activity. RNase and subtilisin activity were measured after an incubation time of 0 min., 1 min., 2 min., 4 min., 6 min., and 8 min. The results are shown in Table 3.

TABLE 3

| RNase activity and subtilisin activity (pH 10.0 and 60° C.) | | | | | | |
| --- | --- | --- | --- | --- | --- | --- |
| Time | 0 min. | 1 min. | 2 min. | 4 min. | 6 min. | 8 min. |
| RNase Activity | 100% | 18% | 3% | 2% | 0% | 0% |
| Subtilisin activity | 100% | 104% | 104% | 106% | 104% | 104% |

Conclusion:
It can be seen from Table 3 that by using the method of the invention it is possible to inactivate the RNase completely and maintain all the subtilisin activity (by using a higher pH but a lower temperature compared with Test B).

The invention claimed is:

1. A method for reducing nuclease activity in a subtilisin-comprising fermentation broth solution, the method comprising:
   a) adjusting the pH of the subtilisin solution to a pH in the range of from pH 8.5 to pH 10.5;
   b) adding a polyol in an amount of 10% (v/v) to 60% (v/v);
   c) adjusting the temperature of the subtilisin-comprising fermentation broth solution to a temperature in the range of from 50° C. to 80° C.; and
   (d) incubating the subtilisin- and nuclease-comprising solution for a period of up to 10 minutes,
   wherein the nuclease activity is reduced to less than 5% of the initial value and the subtilisin activity is maintained at more than 80% of the initial value.

2. The method according to claim 1, wherein the nuclease is a ribonuclease or a deoxyribonuclease.

3. The method according to claim 1, wherein the subtilisin is selected from the group consisting of subtilisin Carlsberg, subtilisin BPN', subtilisin 147, subtilisin 309 and subtilisin 1168.

4. The method according to claim 1, wherein the subtilisin is produced by *Bacillus*.

5. The method according to claim 1, wherein the subtilisin solution is an ultrafiltrated fermentation broth.

6. The method according to claim 1, wherein the pH of the subtilisin solution is adjusted to a pH in the range of from pH 9.0 to pH 10.0.

7. The method according to claim 1, wherein the temperature of the subtilisin solution is adjusted to a temperature in the range of from 60° C. to 70° C.

8. The method according to claim 1, wherein the nuclease activity is reduced to less than 1% of the initial value.

9. The method according to claim 1, wherein the subtilisin activity is maintained at more than 90% of the initial value.

10. The method according to claim 1, wherein the polyol is selected from the group consisting of 1,2-propandiol, 1,3-propandiol, glycerol, ethylene glycol, xylitol, arabitol, dulcitol, mannitol, erythritol, cellobiose and sorbitol.

11. The method according to claim 1, comprising incubating the subtilisin solution for a period of up to 10 minutes.

12. The method according to claim 1, wherein step b) is performed before step a).

13. A method for reducing initial nuclease activity and maintaining subtilisin activity in a subtilisin solution comprising:
   a) adjusting the pH of the subtilisin solution to a pH in the range of from pH 8.5 to pH 10.5,
   b) adding a polyol in an amount of 10% (v/v) to 60% (v/v);
   c) adjusting the temperature of the subtilisin solution to a temperature in the range of from 50° C. to 80° C.; and
   (d) incubating the subtilisin- and nuclease-comprising solution for a period of up to 10 minutes,
   wherein nuclease activity is reduced to at least less than 5% of the initial value and the subtilisin activity is maintained at more than 70% of the initial value.

14. The method according to claim 13, wherein the polyol is selected from the group consisting of 1,2-propandiol 1,3-propandiol, glycerol, ethylene glycol, xylitol, arabitol, dulcitol, mannitol, erythritol, cellobiose and sorbitol.

15. The method of claim 13, wherein polyol is added in an amount of 20% (v/v) to 50% (v/v).

16. The method of claim 13, wherein polyol is added in an amount of 30% (v/v) to 50% (v/v).

17. A method for reducing initial nuclease activity and maintaining subtilisin activity in a subtilisin solution comprising:
   a) providing an ultrafiltrated subtilisin fermentation broth solution at a pH of pH 8.5 to pH 10.5;
   b) adding a polyol in an amount of 10% (v/v) to 60% (v/v);
   c) adjusting the temperature of the subtilisin solution to a temperature in the range of from 50° C. to 80° C.; and
   (d) incubating the subtilisin- and nuclease-comprising solution for a period of up to 10 minutes,
   wherein nuclease activity is reduced to at least less than 5% of the initial value and the subtilisin activity is maintained at more than 70% of the initial value.

18. A method for reducing nuclease activity in a subtilisin solution comprising:
   a) providing an ultrafiltrated subtilisin fermentation broth solution at a pH of pH 8.5 to pH 10.5;
   b) adding a polyol in an amount of 10% (v/v) to 60% (v/v);
   c) adjusting the temperature of the subtilisin solution to a temperature in the range of from 50° C. to 80° C.; and
   (d) incubating the subtilisin- and nuclease-comprising solution for a period of up to 10 minutes,
   wherein the nuclease activity is reduced to less than 5% of the initial value and the subtilisin activity is maintained at more than 80% of the initial value.

19. The method according to claim 18, wherein the nuclease is a ribonuclease or a deoxyribonuclease.

20. The method according to claim 18, wherein the subtilisin is selected from the group consisting of subtilisin Carlsberg, subtilisin BPN', subtilisin 147, subtilisin 309 and subtilisin 1168.

21. The method according to claim 18, wherein the polyol is selected from the group consisting of 1,2-propandiol, 1,3-propandiol, glycerol, ethylene glycol, xylitol, arabitol, dulcitol, mannitol, erythritol, cellobiose and sorbitol.

* * * * *